(12) United States Patent
Speicher et al.

(10) Patent No.: US 6,638,408 B1
(45) Date of Patent: Oct. 28, 2003

(54) METHOD AND DEVICE FOR SEPARATION OF CHARGED MOLECULES BY SOLUTION ISOELECTRIC FOCUSING

(75) Inventors: David W. Speicher, Berwyn, PA (US); Xun Zuo, Upper Darby, PA (US)

(73) Assignee: The Wistar Institute, Philadelphia, PA (US)

(*) Notice: Subject to any disclaimer, the term of this patent is extended or adjusted under 35 U.S.C. 154(b) by 0 days.

(21) Appl. No.: 09/541,520

(22) Filed: Apr. 3, 2000

(51) Int. Cl.[7] .................. B01D 57/02; B01D 59/42; B01D 59/50; B01D 61/42; B01D 61/58; C02F 1/469; C07K 1/26; C08F 2/58

(52) U.S. Cl. .............. 204/458; 204/610; 204/614; 204/418; 204/419; 204/518; 204/527; 204/450; 204/459; 204/523; 204/544; 204/644; 204/627

(58) Field of Search .................. 204/610, 614, 204/600, 418, 419, 403.06, 403.07, 450, 459, 518, 527, 523, 530, 540, 541, 543, 544, 644, 666, 627; 205/778

(56) References Cited

U.S. PATENT DOCUMENTS

| | | | | |
|---|---|---|---|---|
| 3,844,925 A | * | 10/1974 | Stathakos | 204/610 |
| 4,204,929 A | * | 5/1980 | Bier | 204/518 |
| 4,243,507 A | * | 1/1981 | Martin et al. | 204/296 |
| 4,608,147 A | * | 8/1986 | Clad | 204/613 |
| 4,673,483 A | * | 6/1987 | Mandle | 204/627 |
| 4,971,670 A | | 11/1990 | Faupel et al. | |
| 5,039,386 A | * | 8/1991 | Margolis | 204/466 |
| 5,082,548 A | | 1/1992 | Faupel et al. | |
| 5,336,387 A | * | 8/1994 | Egen et al. | 204/627 |
| 5,540,826 A | * | 7/1996 | Bier et al. | 204/610 |
| 6,171,466 B1 | * | 1/2001 | Rhodes et al. | 204/600 |

FOREIGN PATENT DOCUMENTS

WO   WO 00/17631   3/2000

OTHER PUBLICATIONS

PCT International Search Report for PCT/US 01/10012 dated Apr. 18, 2002.
XP 000653568, Righetti et al., "Preparative Protein Purification in a Multi–Compartment Electrolyser with Immobiline Membranes", Journal of Chromotography, vol. 475 (1989) pp. 293–309.
XP0029062101, Corthals et al., "Prefractionation of protein samples prior to two–dimensional electrophoresis", Electrophoresis 1997, vol. 18, pp. 317–323.
XP–000870391, Quadroni et al., "Proteomics and automation", Electrophoresis 1999, vol. 20, pp. 664–677.
Righetti et al. (1989) J. Chromatogr. 475:293–309.
Righetti et al. (1990) J. Chromatogr. 500:681–696.
Corthals et al. (2000) Electrophoresis 21(6):1104–1115. (According to the publisher, this journal issue was mailed to subscribers on Apr. 11, 2000, and was posted on the World Wide Web on Apr. 17, 2000).
Hoefer IsoPrime IEF Purification Unit User Manual (2–99).

* cited by examiner

*Primary Examiner*—Mark L. Bell
*Assistant Examiner*—Jennine Brown
(74) *Attorney, Agent, or Firm*—Banner & Witcoff, Ltd.

(57) ABSTRACT

The invention provides a novel solution isoelectric focusing device and method that can reproducibly fractionate charged molecules into well-defined pools. This approach can be applied to mixtures of charged molecules, such as eukaryotic proteome samples where reproducible resolution and quantitation of greater than 10,000 protein components is feasible.

33 Claims, 9 Drawing Sheets

FIG. 7
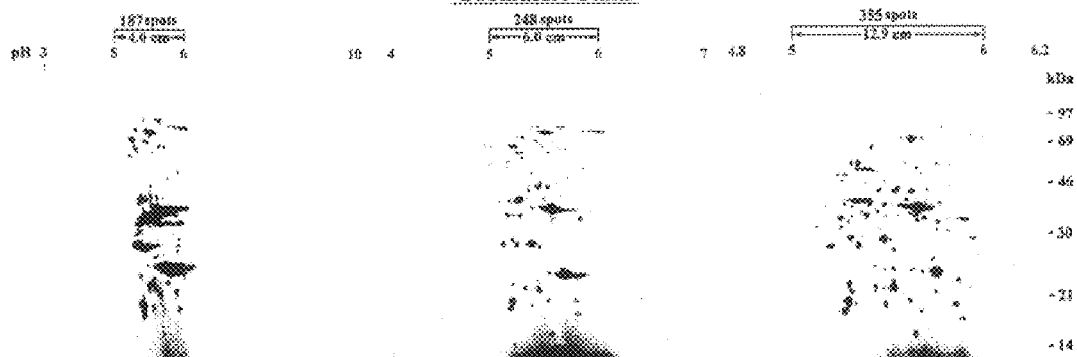
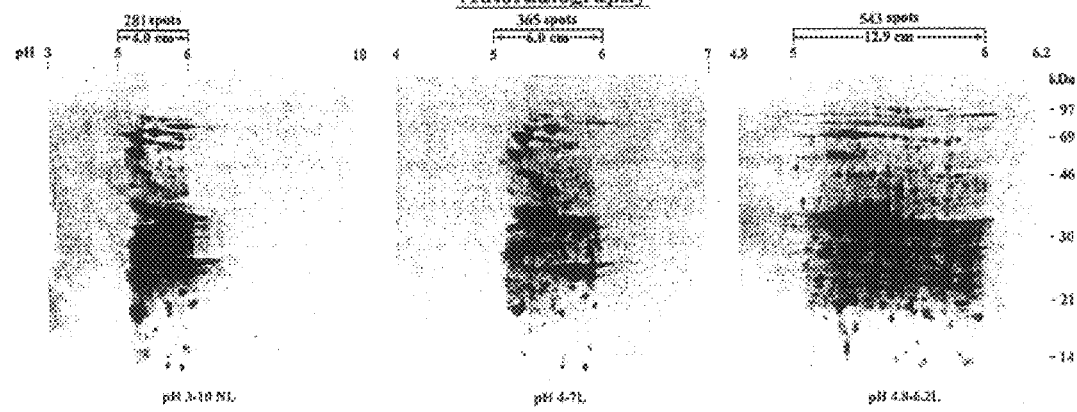

METHOD AND DEVICE FOR SEPARATION OF CHARGED MOLECULES BY SOLUTION ISOELECTRIC FOCUSING

STATEMENT OF GOVERNMENT INTEREST

This invention was made with government support under NIH Grant No. RO1 CA77048 and RO1 CA66671. As such, the government has certain rights in this invention.

TECHNICAL FIELD OF THE INVENTION

The invention relates to the field of separation of charged molecules, and in particular the separation of mixtures of charged molecules.

BACKGROUND OF THE INVENTION

Complex charged molecule mixtures, such as protein mixtures can be separated by isoelectric focusing under denaturing conditions in gel tubes or strips that contain either soluble ampholytes (Klose, (1975) Humangenetik 26, 231–243; O'Farrell, (1975) *J. Biol. Chem.* 250, 4007–4021; Scheele, (1975) *J. Biol. Chem.* 250, 5375–5385) or immobilines (Bjellqvist et al. (1982) *J. Biochem. Biophys. Meth.* 6, 317–339). For quantitative comparisons in changes in total protein profiles a second dimension separation can be done on a conventional SDS polyacrylamide gel electrophoresis (PAGE) slab gel.

Current two dimensional (2D) methods, however, lack both adequate resolution and sufficient dynamic range for resolving and detecting large numbers of charged molecules, for example, the protein components present in eukaryotic proteomes which can comprise over 10,000 proteins. A major disadvantage of existing 2D gel methods when applied to a large number of charged molecules is that the maximum sample loading capacity is fairly low, which results in detection of only the most abundant charged molecules when currently available stains are used (Herbert et al. 1997; Williams 1999; Quadroni et al. 1999). Increasing the amount of sample above an optimal level results in horizontal streaking of many proteins. Although current IPG-based 2D gels have much higher resolution than alternative separation methods, not all charged molecules in a sample can be resolved by a single IPG gel. This incomplete resolution contributes to errors in subsequent quantitation and identification of charged molecules. Hence, effective analyses of complex charged molecule mixtures such as extracts from eukaryotic cells or tissues require improved separation methods capable of resolving and quantitatively detecting thousands of components.

One method for resolving a large number of charged molecules is prefractionation of sample proteins prior to further analysis. Previously reported prefractionation methods prior to 2D PAGE include sequential extractions with increasingly stronger solubilization solutions (Molloy et al. (1998) *Electrophoresis* 19, 837–844), subcellular fractionation (Huber et al. (1996) *Electrophoresis* 17, 1734–1740) and selective removal of the most abundant components (Lollo et al. (1999) *Electrophoresis* 20, 854–859). Other alternatives include conventional chromatography techniques, such as gel filtration, ion exchange, or affinity chromatography. The use of these methods, however, can result in an incomplete separation of charged molecules between fractions and a poor yield. Using current methods cross contamination of specific charged molecules between fractionated pools can seriously complicate quantitative analyses and comparisons, since many charged molecules appear in more than one fraction and the degree of cross contamination is often highly variable.

Preparative isoelectric focusing as a protein prefractionation procedure was proposed by Bier et al. (in: Peptides: Structure and Biological Functions (Gross & Meienhofer, eds., pp.79–89, Pierce Chemical Co., Rockford, Ill., 1979) and a commercial version called Rotofor™ was produced by Bio-Rad (Hercules, Calif., USA). It is built as a rotating chamber divided into 20 compartments and uses solution isoelectric focusing to fractionate samples. However, this apparatus has no separation barriers and is typically a low resolution technique with relatively large volumes for individual fractions. Righetti et al. ((1989) *J. Chromatogr.* 475, 293–309) described a multi-compartment electrolyser in which each compartment is separated by a polyacrylamide gel membrane with a specific pH produced by immobilines that are incorporated into the polyacrylamide membranes. A commercial apparatus, called IsoPrime™, incorporating this principle has been marketed (Hoefer Pharmacia, San Francisco, Calif.). The IsoPrime™ unit has been developed primarily for large scale purification of individual proteins starting with partially purified preparations, not for fractionation of crude extracts. The unit has large separation chambers connected to peristaltic pumps and external chambers to further expand the volumes of individual fractions (about 30 ml). While the IsoPrime™ unit can provide high quality separations, its large volume and design make it impractical for prefractionation of samples containing complex mixtures of charged molecules, especially under denaturing conditions. Similarly, other preparative isoelectric focusing instruments suffer from at least several of the limitations encountered with either the Rotofor™ or the IsoPrime™; specifically these instruments: (1) require a large sample volume, (2) produce large volume, dilute fractions that need to be concentrated with attendant losses, (3) exhibit poor resolution, or (4) involve expensive, complex instrumentation.

Better prefractionation methods for the separation of large numbers of charged molecules should improve the detection of minor charged molecules occurring in a mixture and increase the total number of protein components that can be identified (Quadroni & James, (1999) *Electrophoresis* 20, 664–677; Williams (1999) *Electrophoresis* 20, 678–688). The ideal prefractionation method would resolve complex mixtures such as total extracts of eukaryotic cells or tissues into a small number of well-separated fractions.

SUMMARY OF THE INVENTION

It is an object of the invention to provide a novel device and method for the separation of mixtures of charged molecules. These and other objects of the invention are provided by one or more of the embodiments described below.

One embodiment of the invention provides a chamber for holding a liquid. The chamber has a first porous charged membrane partition or a first membrane permeable to small ions at a first end and a second porous charged membrane partition or a second membrane permeable to small ions at a second end which is opposite the first end. The chamber also has at least one porous charged membrane partition positioned along the chamber to define a plurality of compartments within the chamber such that each compartment holds a volume of liquid less than about 4 ml.

Another embodiment of the invention provides a chamber for holding a liquid. The chamber has a first porous charged membrane partition or a first membrane permeable to small ions at a first end and a second porous charged membrane partition or a second membrane permeable to small ions at a second end which is opposite the first end. The chamber also has means for separating a mixture of at least ten species of charged molecules in liquid.

Yet another embodiment of the invention provides a method of separating a mixture of charged molecules. A mixture of charged molecules in solution is added to a chamber as described above and a direct current is applied between the first end and the second end of the chamber. The charged molecules are separated.

Still another embodiment of the invention provides a method of separating a mixture of at least about 10 species of charged molecules in liquid. The charged molecules are added to a chamber for holding liquid having a first porous charged membrane partition or a first membrane permeable to small ions at a first end and a second porous charged membrane partition or a second membrane permeable to small ions at a second end which is opposite the first end. At least one porous charged membrane partition is positioned along the chamber to define a plurality of compartments within the chamber. A direct current is applied between the first end and the second end of the chamber, whereby the charged molecules are separated.

This invention provides a novel small-scale solution isoelectric focusing device and method that can reproducibly fractionate charged molecules into well-defined pools. This approach can be applied to complex charged molecule samples, such as eukaryotic proteome samples where reproducible resolution and quantitation of greater than 10,000 protein components is feasible.

BRIEF DESCRIPTION OF THE FIGURES

FIG. 7 Demonstrates the effects of IPG strip pH ranges on protein resolution. Replicate pH 5–6 range samples (proportional to 1 mg of unfractionated *E. coli* extract), which were prefractionated using solution isoelectric focusing, were focused using pH 3–10 NL, 4–7 L and 4.8–6.2 L IPG strips, respectively, followed by separation in 10% SDS-gels. Proteins were visualized using Coomassie blue staining (upper panels) and autoradiography (lower panels). Spots were detected and counted using Melanie II software. These values and the effective separation distances for proteins with pI between 5 and 6 are shown above each 2D gel.

DETAILED DESCRIPTION OF THE INVENTION

Charged molecules, including proteins, can be separated using isoelectric focusing by virtue of their different net charges at a particular pH. The invention provides a novel device and method of solution isoelectric focusing of charged molecules and is especially useful for the separation of a mixture comprising a number of charged molecules. The invention is particularly useful for prefractionation of a complex protein mixture prior to two-dimensional electrophoretic separation, chromatography, and/or mass spectrometry of the proteins.

The Chamber

Figure 1:
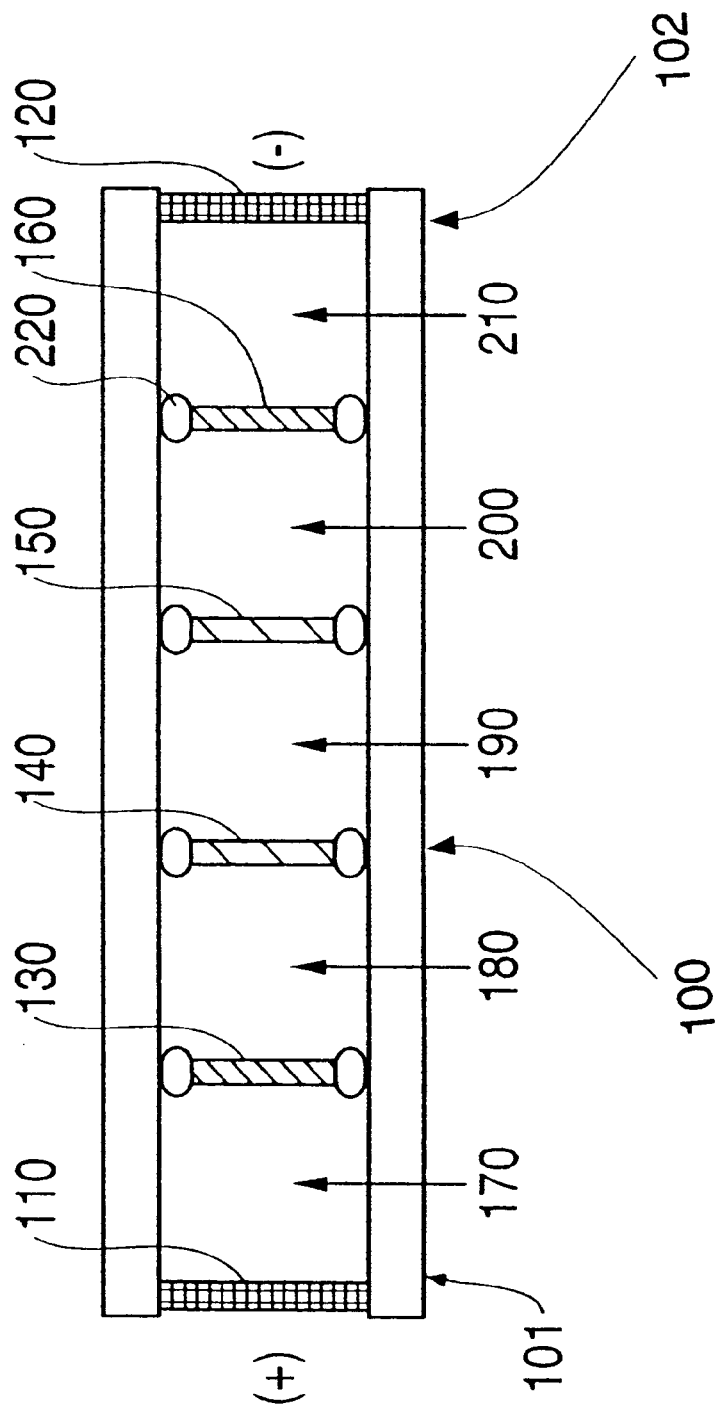
FIG. 1 Shows a schematic illustration of one embodiment of a solution isoelectric focusing device.

The invention comprises a chamber for holding liquid. As shown in FIG. 1, an embodiment of the invention comprises a chamber (100). A porous charged membrane partition or membrane permeable to small ions (110) is located at a first end of the chamber (101). Another porous charged membrane partition or membrane permeable to small ions (120) is located at a second end of the chamber (102), opposite of the first end of the chamber (101). The membranes permeable to small ions (110, 120) are partitions. Porous charged membrane partitions (130, 140, 150, 160) are positioned along the chamber (100) to define a plurality (i.e., 2 or more)

of compartments (170, 180, 190, 200, 210) within the chamber (100). The membrane partitions (130, 140, 150, 160) are each fitted into the chamber (100) with a seal (220). While four membrane partitions (130, 140, 150, 160) are shown in FIG. 1, any number of membrane partitions can be used.

In an alternative embodiment of the invention the compartment formed by the porous charged membrane partition or membrane permeable to small ions (110) at the first end of the chamber (101) and the adjacent porous charged membrane (130) is a terminal buffer compartment (170) and is filled with anode buffer. Additionally, the compartment formed by the porous charged membrane partition or membrane permeable to small ions (120) at the second end of the chamber (102) and the adjacent porous charged membrane (160) is a terminal buffer compartment (210) and is filled with cathode buffer.

Optionally, where the porous membrane partitions comprise polymer gels, a gel membrane partition (130) adjacent to the porous charged membrane partition or membrane permeable to small ions (110) at the first end of the chamber (101) and a gel membrane partition (160) adjacent to the porous charged membrane partition or membrane permeable to small ions (120) at the second end of the chamber (102) comprise a higher percentage of polymer than the remaining gel membrane partitions. In this optional embodiment, the compartment formed by the porous charged membrane partition or membrane permeable to small ions (110) at the first end of the chamber (101) and the adjacent gel membrane (130) is a terminal buffer compartment (170) and is filled with anode buffer. Further, the compartment formed by the porous charged membrane partition or membrane permeable to small ions (120) at the second end of the chamber (102) and the adjacent gel membrane (160) is a terminal buffer compartment (210) and is filled with cathode buffer.

The chamber (100) can comprise any suitable material for holding a liquid and for use in an electrophoresis tank, for example, teflon, glass, or plastic. The chamber comprises a porous charged membrane partition or membrane permeable to small ions (110) at a first end of the chamber (101) and at a second end of the chamber (102), opposite of the first end. The porous charged membrane partitions or membranes permeable to small ions (110, 120) provide protection for the compartments within the chamber. A membrane permeable to small ions can have a molecular weight cut-off of, for example, at least about 1, 5, 10, or 30 kDa; however, the use of membranes with any molecular weight cut-off is contemplated by the invention. The porous charged membrane partitions or membranes permeable to small ions at the first and second ends of the chamber can also prevent proteins with isoelectric points (pI) beyond the pH range of the separation compartments from migrating out of the chamber. An example of a useful membrane permeable to small ions for the ends of the chamber is a dialysis membrane.

The chamber is divided into separation compartments by porous charged (i.e., positively or negatively charged) membrane partitions. Preferably, the partitions comprise covalently linked buffering groups. A porous membrane partition can comprise an organic or an inorganic membrane or polymers thereof. A membrane can comprise, for example, polyacrylamide, agarose, acrylamide-agarose copolymers, or other suitable polymer. Where the porous membrane partition comprises a membrane filter, for example a glass membrane filter, the pore size is preferably less than 0.5 microns. Even more preferably, the pore size is 0.22 microns or less. A chamber can comprise partitions where each partition is made of the same material or a chamber can comprise partitions where one or more partitions are made of different materials than the remaining partitions.

Where a porous charged membrane partition comprises polyacrylamide the concentration of acrylamide in the membrane partition is stated generally in terms of %T (the total percentage of acrylamide in the gel by weight) and %C (the proportion of the total acrylamide that is accounted for by the crosslinker used). N,N'-methylenebisacrylamide ("bis") is an example of a crosslinker that can be used. Preferably, a gel membrane partition has a large pore size that does not obstruct the movement of charged molecules through or within the gel membrane partition. One of skill in the art can use only routine experimentation to construct a gel membrane partition comprising a suitable %T and %C. Useful gel membrane partitions can comprise at least about 1, 3, 10, 15, or 25%T and at least about 1, 5, 8, 15, or 25% C.

Preferably, each porous charged partition comprises a pH different from any other membrane partition within a chamber. A membrane partition can comprise any pH suitable for the separation of charged molecules. Even more preferably, each membrane partition comprises a different pH such that a range of pH's are represented by the membrane partitions in the chamber. One of skill in the art can select membrane partitions representing a range of pH's that would be useful to fractionate a particular set of charged molecules. Where the membrane partitions each comprise a different pH, the membrane partitions are preferably arranged sequentially from lowest to highest pH within a chamber. The pH of a membrane partition can be adjusted to the desired pH by covalently linking buffering groups to the membrane partition. Suitable buffering groups include, for example, immobilines (Fluka Chemical Co., Milwaukee, Wis.).

Immobilines are acrylamide derivatives with the general structure:

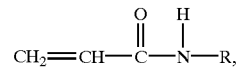

where R comprises either a carboxylic acid or a tertiary amino group. Immobilines can be co-polymerized with a polymer for example, acrylamide, methacyrlamide or other polymer and N,N'-methylene-bis-acrylamide or other crosslinker. Immobilines can also be crosslinked to porous membrane filters. Immobilines become covalently bound to the porous membrane partition and do not contribute or interfere with the conductivity of the membrane partition but do contribute to the buffering and titrant capacity of the membrane partition.

A porous membrane partition can be, for example, about 0.01, 1, 5 mm or more thick. The area of a membrane partition can be about 10 $mm^2$, 100 $mm^2$, 250 $mm^2$, 500 $mm^2$, or more. Preferably the area of a membrane is between about 5 and 200 $mm^2$. A membrane partition can comprise any shape that will fit within a chamber, for example, a square or a circle. Any number of membrane partitions can be used in the chamber to form any number of compartments within the chamber. For example, at least 1, 4, 10, 50, 100, or more membrane partitions can occur in a chamber to form a plurality of compartments. In a preferred embodiment of the invention 4 or 6 membrane partitions are used to form 5 or 7 compartments.

A polymer gel membrane partition can be mechanically strengthened by embedding a highly porous matrix within the gel membrane partition. For example, non-glass fiber filters or glass fiber filters, such as Whatman GF/D, glass fiber filters can be used to strengthen a gel membrane partition.

A membrane partition is sealed into a chamber of the invention so that no leakage of liquid or current occurs between the compartments formed by membrane partitions. A membrane partition can be, for example, fitted into an O-ring or encircled with rubber tubing such that a seal is formed between the O-ring or tubing and the chamber. Alternatively, a gel membrane partition can be cast within a gasket comprising a suitable material, such as teflon or polypropylene. The gasket comprising a gel membrane partition is fitted into the chamber such that a seal is formed between the gasket and the chamber.

The volume of liquid held by each compartment of the chamber is less than 5 ml. Preferably, the volume of the liquid held by each compartment is less than about 4 ml, 2 ml, 1 ml, or 0.1 ml. In a preferred embodiment of the invention the volume of the liquid held by each compartment is about 0.5 ml.

Optionally, each compartment of the chamber can comprise an access port (230, FIG. 8), which can be used to insert or extract liquid from each individual compartment. Preferably, the port allows a syringe or pipette tip access to a compartment such that liquid can be added to or removed from each compartment.

Optionally, the chamber can be agitated to provide for movement of liquid within the compartments. The chamber can be agitated by, for example, a magnetic stirrer or by rotating the chamber in a circular fashion.

In a preferred embodiment of the invention an apparatus is provided comprising a chamber, as described above, a tank for electrophoresis, and a power source. Other embodiments of the invention provide an apparatus comprising a chamber and a power source or a chamber and an electrophoresis tank. A chamber is set into a electrophoresis tank and the tank is filled with anode and cathode buffers. If the chamber comprises terminal buffer compartments, these compartments are also filled with anode and cathode buffers. The separation compartments are filled with a sample or buffer. A power source is connected to the tank and a voltage is applied.

Methods of Separating Charged Molecules

A chamber as disclosed above can be used to separate charged molecules. The charged molecules migrate under an applied electric current through the chamber until the charged molecule enters a region of the chamber, i.e., a compartment or a membrane partition, where the charged molecule has a net charge of zero, i.e., at the charged molecule's isoelectric point (pI), or the charged molecule enters a compartment where the boundary membrane partitions have pH's that are less than and greater than the charged molecule's isoelectric point. For example, a protein with a pI of 5.5 will migrate into and remain within a separation compartment bordered by membranes with pH's of 5.0 and 6.0, respectively. The charged molecules can be a mixture of about at least 10, 100, 1,000, 10,000, 15,000, or more different types (or species) of molecules. Preferably, the charged molecules are proteins. For example, the charged molecules can be a prokaryotic or a eukaryotic proteome (the expressed protein complement of a genome) or a subset or fraction thereof, a cell or tissue extract or a fraction thereof, such as a nuclear fraction, or a biological fluid, such as serum, plasma, urine, sputum, colonic effluent, bone marrow, is lymph, and cerebrospinal fluid. A proteome can comprise about 1,000, 10,000, 15,000, or more protein components. A biological fluid can comprise about 100, 500, 1,000, or more protein components.

Any preparation of charged molecules can be separated by the device and method of the invention. Examples of charged molecules include, but are not limited to proteins, nucleic acids, protein-nucleic acid complexes, and protein-ligand complexes. Samples can be crude or can be partially purified. A protein sample is preferably denatured. A device and method of the invention are particularly useful for the analysis of a proteome.

Eukaryotic or prokaryotic protein samples can be prepared, for example, by obtaining a population of prokaryotic cells or eukaryotic cells from, for example, cell culture or a tissue sample, and lysing the cells by procedures well known in the art. For example, cells can be pelleted and resuspended in lysis buffer followed by, for example, sonication of the cells. See e.g., Ausubel et al (1994) CURRENT PROTOCOLS IN MOLECULAR BIOLOGY, (Greene Publishing Associates and John Wiley & Sons, New York, N.Y.), and Sambrook et al. (1989), MOLECULAR CLONING: A LABORATORY MANUAL, 2nd ed. (Cold Spring Harbor Press, Cold Spring Harbor, N.Y.). After sonication, the cell lysate can be subjected to denaturing agents or detergents and centrifuged. The amount of total protein in a sample can be determined using, for example a BCA protein assay (Pierce Chemical Co. Rockford, Ill., USA). The samples can be further treated with DNase/RNase to digest the nucleic acids (Harper & Speicher, (1995) in Current Protocols in Protein Science (Coligan et al., eds.), pp. 10.4.1–10.4.36, John Wiley & Sons Inc., Virginia)).

A charged molecule sample is mixed or solubilized with a liquid such as IPG sample buffer and added to at least one separation compartment. IPG sample buffer can be added to any separation compartment not receiving the charged molecule sample. Preferably, the sample in AS IPG buffer is divided equally by the number of separation compartments and placed into each of the compartments. Where the sample is a protein or mixture of proteins about 0.01, 1, 10, 50 mg or more of protein can be loaded into each separation compartment. If a chamber comprises terminal buffer compartments, these compartments are filled with isoelectric focusing anode and cathode electrode buffers. These buffers can be made by one of skill in the art and are also commercially available (BioRad Laboratories, Hercules, Calif.; Invitrogen, Carlsbad, Calif.).

The filled chamber can be placed into an electrophoresis tank and each of the two compartments of the tank filled with anode and cathode buffers. A power supply can be attached to the electrophoresis tank and voltage applied until the current drops to low and stable levels indicating that equilibrium has been reached as is known in the art. Typically, a direct current of at least 25, 100, 500, 1,000, or 2,000 V can be used for 1, 12, 24, or 48 hours. Optionally, the voltage can be adjusted throughout the focusing until the current drops to low levels.

After equilibrium has been reached, a fractionated sample is removed from each separation compartment. In order to recover a greater portion of the fractionated sample, the surfaces of the porous membrane partitions and the inside walls of the separation compartments can be rinsed with a small amount of a sample buffer and the rinse combined with the fractionated samples. Even greater recovery of the fractionated sample can be accomplished by removing each membrane partition from the chamber and extracting any charged molecules from the membrane. These extracted charged molecules can be either analyzed separately or combined with a fractionated sample, most preferably these extracted charged molecules are combined with a fractionated sample that was recovered from a compartment on either side of the particular membrane partition that was extracted. Additionally, charged molecules can be a recovered from the terminal buffer compartments, if present, and either analyzed separately or combined with the fractionated sample derived from the compartment adjacent to the terminal buffer chamber. Preferably about 50, 80, or 95% of the total amount of proteins or charged molecules added to the chamber are recovered as fractionated samples.

Figure 9:
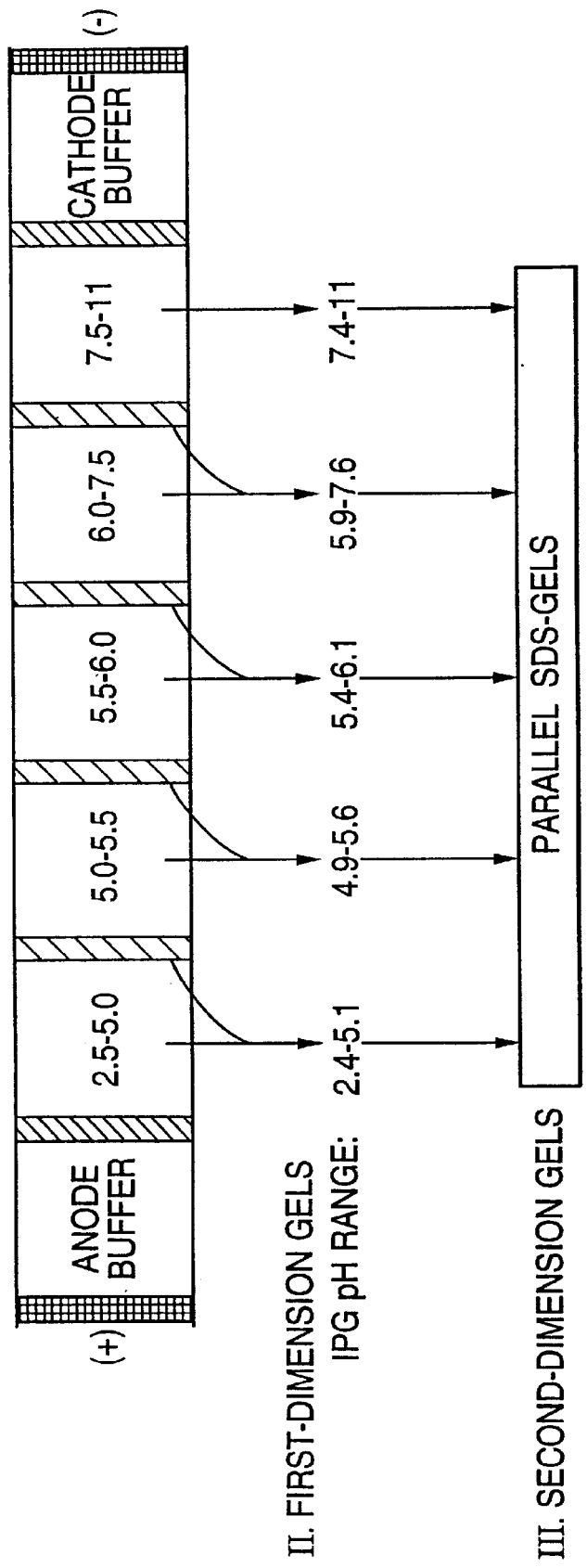
FIG. 9. Shows a schematic illustrating a method for global analysis of complex charged molecule mixtures, such as eukaryotic proteomes or biological fluids. The specific number of separation compartments and the pH's of the separation membrane partitions can be adjusted to fit different conditions and sample properties. It should be feasible to optimize the pH ranges so that the full resolving capacity of each gel can be utilized. Since each full sized (18 cm×20 cm) gel should be readily capable of resolving 2,000 to 3000 spots when a high sensitivity detection method is used, the illustrated scheme should be capable of resolving on the order of 10,000 to 15,000 protein spots when complex eukaryotic proteomes are analyzed.

Once the charged molecule sample is fractionated it can be, for example, separated by SDS PAGE. Alternatively, fractionated samples prepared using solution isoelectric focusing can be separated on different pH range IPG strips or soluble ampholyte isoelectric focusing gels (IEF) gels (Invitrogen, Carlsbad, Calif.) followed by SDS PAGE. For example, a strategy for the global analysis of eukaryotic proteomes is illustrated in FIG. 9. A complex sample is fractionated into approximately five pools by solution isoelectric focusing. The pH ranges of each pool should be selected so that similar numbers of spots are obtained on each subsequent 2D gel. For example, in the illustrated embodiment (FIG. 9) the pH 5–6 range has been divided into 0.5 pH unit increments since the largest proportion of proteins in eukaryotic proteomes typically fall in this pH range. As described above proteins with pI's equal to the porous membrane partitions are retained on or in the partition and can be recovered in reasonable yields by extraction with a small volume of sample buffer. The proteins eluted from the membrane partition can then be combined with the adjacent solution fraction to minimize sample losses at these boundaries.

Fractionated samples are then loaded onto narrow pH range gels. Preferably, the gels are about 0 to 0.2 pH units wider than the flanking gel membranes. Parallel SDS-gels are used for second-dimension separation electrophoresis. The ability to increase the protein load per narrow pH range gel using prefractionated samples compared with unfractionated samples can improve the dynamic range of the global proteome analysis by permitting detection of less abundant spots for any given detection method and by increasing separation distances between minor components and major components. In addition, the prefractionation step more efficiently utilizes samples available in limited amounts compared with analysis of unfractionated samples on narrow pH range gels. Since each narrow pH range gel has the capacity to resolve approximate 2,000 to 3,000 protein components, the one embodiment outlined in FIG. 9 showing the separation of a sample into five fractions to be loaded onto five overlapping narrow pH range gels provides a robust method for reliably detecting at least 10,000–15,000 protein components. Of course, the total number of separation compartments can be either increased or decreased to fit requirements of specific studies.

Optionally, a charged molecule sample fractionated by the device and method of the invention can be analyzed by a chromatography instrument, such as a HPLC instrument, that uses a mass spectrometer as a detector (LC/MS). For example, a fractionated sample is directly injected or preferably fragmented with a protease or chemical cleavage method prior to injection onto a reversed-phase HPLC column, and eluted with a gradient of increasing organic solvent into the source of an electrospray ionization interface mass spectrometer, for example an ion trap MS or a triple quadropole MS. For example, when using an ion trap MS, the liquid effluent is converted into an aerosol and solutes in the aerosol are ionized. Desolvated ions are drawn into the analyzer of the mass spectrometer by voltage gradients and are collected in a trap. Once the trap is filled, the voltages are varied so that ions leave in an orderly, mass-dependent manner and strike a detector. By calibrating the instrument with ions of known mass, unknown masses of samples can be measured.

Further, specific ions can be isolated in the trap and fragmented by collision-induced dissociation, and the masses of the fragments measured by LC/MS/MS instrument, for example a Finnegan LCQ quadropole mass spectrometer. For a peptide, most fragmentation occurs at peptide bonds resulting in fragmentation patterns that contain information about the peptide. See Yates et al. (1997) *J. Protein Chem.* 16, 495. This information can be used to identify a protein or proteins in a sample. For example, the computer program SEQUEST can match fragmentation patterns to those predicted from sequences in databases. Proteins are identified when several peptides from a sample are matched to the same database entry with above-threshold scores.

A charged molecule sample can be fractionated into about 10, 20, 50, or more fractions using the device and method of the invention for analysis by the LC/MS methods described above. Preferably, the concentration of detergent is low, i.e., about 0.1% to 1.0%, such that charged molecules, such as peptides, can efficiently bind to the column, and the volume of each separation compartment is low, i.e., about 100 $\mu$l to 300 $\mu$l. At least one fraction is fragmented using, for example, proteases such as trypsin or chemical cleavage. An aliquot of a cleaved fraction is loaded onto a capillary reverse phase column. The column is introduced into the flow pathway of a capillary HPLC interfaced with a mass spectrometer equipped with an electrospray interface. Charged molecule masses and MS-MS spectra are obtained by established methods, and are used to identify the charged molecules utilizing database search algorithms such as the program SEQUEST.

Quantitative comparisons of charged molecule levels in corresponding solution isoelectric focusing fractions between two or more starting samples, i.e., proteomes, biological fluids, cell or tissue samples, can be accomplished using the device and methods of the invention. Corresponding solution isoelectric focusing fractions are obtained by subjecting two or more samples to the method of the invention using for each sample a device of the invention that has the same type and pH porous membrane partitions. Corresponding fractions are obtained by to collecting the same fraction, e.g., the pH 4.5 to 5.0 fraction, for each sample. These corresponding fractions are separately fragmented using a protease or chemical cleavage method followed by analysis using LC/MS or LC/MS/MS methods as described above. Optionally, two or more different samples can be differentially labeled with chemical groups using cysteine reactive reagents or reagents that target other amino acids prior to separation by solution isoelectric focusing or immediately after solution isoelectric focusing. Greg T. Hermanson, Bioconjugate Techniques, 3–21 Academic Press, San Diego (1996). For example, differential isotopic labels as reported by Gygi et al. can be used to label fractions (*Nat. Biotechnol.* 17, 994 (1999). Multiple sample labeling reactions preferably use related labeling reagents that have similar reactivities to the targeted amino acids and have sufficiently different masses that can be distinguished by a mass spectrometer.

After labeling, the two or more samples are combined and fragmented with enzymes or chemical cleavage methods. An aliquot of this sample is analyzed by chromatography, for example HPLC, coupled to a mass spectrometer. Preferably the mass spectrometer has MS-MS capacity. Signal ratios for all peaks from a given protein can be averaged and ratios calculated using the SEQUEST program to determine relative protein amounts in each of the two or more samples.

The following are provided of exemplification purposes only and are not intended to limit the scope of the invention described in broad terms above. All references cited in this disclosure are incorporated herein by reference.

EXAMPLES

Example 1
Preparation of Metabolically Radiolabeled *Escherichia coli* Extracts Metabolically radiolabeled *E. coli* extracts were used in these studies to systematically evaluate protein recoveries. *E. coli* was selected since this relatively simple organism can be readily metabolically radiolabeled to high specific activity to provide sensitive and reliable detection of protein losses. In contrast to chemical labeling methods such as iodination of a portion of the sample, metabolic radiolabeling of the entire sample ensured that the labeling method would not alter the properties of the proteins and that each protein was a homogeneous population of molecules.

*E. coli* were cultured as previously described (Harper & Speicher, (1995) in Current Protocols in Protein Science (Coligan et al., eds.), pp. 6.6.1–6.6.21, John Wiley & Sons Inc., New York) with modifications. Briefly, *E. coli* cells were inoculated in Luria broth (LB medium) and incubated at 37° C. with continuous shaking (250–300 rpm) for about 6 h. The LB culture was then inoculated into minimal medium and incubated overnight. When the optical density in the overnight culture reached approximately 1.0 at 550 nm, the culture was diluted 9-fold with methionine- and cysteine-free minimal medium containing 5 µCi/ml of Pro-Mix $^{35}$S (Amersham Corp). The cells were cultured until the $OD_{550}$ reached 0.9–1.0 to metabolically radiolabel cell proteins to high specific activity.

The *E. coli* were lysed to extract $^{35}$S-radiolabeled proteins essentially as previously described by Harper & Speicher (1995). Briefly, the cell culture was harvested by centrifugation at 4000 g at 4° C. for 20 min and the cell pellet was resuspended in fresh minimal medium and washed once by centrifugation. After the supernatant was discarded, the pellet was resuspended in 5 ml of lysis buffer containing 50 mM NaCl, 50 mM Tris, 5 mM EDTA, 1 µg/ml leupeptin, 1 µg/ml pepstatin, 0.15 mM phenymethylsulfonyl fluoride (PMSF), 1 mM diisopropyl fluorophosphate (DFP), pH 8.0 and was sonicated on ice using a probe-tip sonicator at the lowest power setting for 20 cycles of 15 sec each with a 1 min hold between sonication cycles to prevent overheating. The cell lysate was centrifuged at 48,000 g at 4° C. for 20 min and the supernatant was retained. SDS was added to the *E. coli* extract supernatant to a final concentration of 0.05%. The sample was dialyzed with two buffer changes for about 15 h at 4° C. against the lysis buffer containing 0.05% SDS using 12 kDa cut-off dialysis membranes to remove unincorporated radiolabel. After the amount of protein in the dialyzed sample was determined using the BCA protein assay (Pierce Chemical Co., Rockford, Ill., USA), samples in aliquots were stored at −80° C. until required. Immediately before use, samples were thawed, treated with DNase/RNase as described by Harper et al. ((1995) in Current Protocols in Protein Science (Coligan et al., eds.), pp. 10.4.1–10.4.36, John Wiley & Sons Inc., Virginia), lyophilized, and dissolved in appropriate IPG sample buffers described in individual experiments and known to those of skill in the art.

Example 2
Two-dimensional Electrophoresis

Isoelectric focusing equipment, IPG gels, and relevant reagents were purchased from Amersham Pharmacia Biotech (San Francisco, Calif., USA), unless otherwise indicated. Proteins were isofocused using different pH range IPG strips (pH 3–10 NL, 4–7 L and 4.8–6.2 L, 18 cm length) on the IPGphor™ Isoelectric Focusing System. Narrow pH range PG gels (pH 4.8–6.2 L) were cast in the laboratory using commercial immobilines as detailed in the IPG application manual. Immediately prior to isoelectric focusing, dried IPG strips were rehydrated for 8 h with sample in IPG sample buffer (350 µl) in the ceramic strip holders (1 h without current followed by 7 h at 30 Volts) as described by Görg et al. (1999) *Electrophoresis* 20, 712–717. The IPG sample buffer contained 2 M thiourea, 7 M urea, 0.1 M DTT, 4% CHAPS and 2% IPG-buffer (carrier ampholyte mixture matching the pH range used). After the 8 h rehydration, samples were focused for 1 h each at 500 V, 1000 V, and 2000 V, respectively, followed by 8000 V for a total of 60 kVh.

Immediately prior to loading focused IPG strips on second-dimension gels, the IPG strips were incubated in 10 ml of 50 mM Tris, 6 M urea, 2% SDS, 30% glycerol, 30 mM DTT, pH 6.8, for 10 min, followed by incubation for 10 min in the same solution, except that the DTT was replaced by 2.5% iodoacetamide. The second-dimension SDS-PAGE was performed in 10% acrylamide separating gels prepared as described by Laemmli ((1970) *Nature* 227, 680–685) using the Iso-Dalt gel format (25×20 cm, 1.5 mm thickness) (Pharmacia). The SDS-equilibrated IPG gel was sealed on top of the second-dimension gel using 0.5% agarose containing 50 mM Tris-Cl (pH 6.8), 2% SDS, 30% glycerol and bromophenol blue. SDS gels were run overnight (at 10 ° C.) until the tracking dye was within 1 cm of the gel bottom. The 2D gels were typically stained using Coomassie Blue R250. In some experiments, autoradiography was also used to visualize radiolabeled proteins. Briefly, gels were fixed in 10% acetic acid, 30% methanol for 1 h, incubated with EN$^3$HANCE™ autoradiography Enhancer (NEN Products, Boston, Mass., USA) for 1 h and dried under vacuum with heat (60–80 ° C.). The dried gel was exposed to a pre-flashed BioMax MS film using a Transcreen-LE Intensifying Screen (Eastman Kodak Company, Rochester, N.Y., USA.) at −80° C. for 1.5–7 h. The 2D gels were analyzed using Melanie II 2-D PAGE analysis software (Bio-Rad).

Example 3
Determination of Protein Recoveries

Protein recoveries and losses throughout alternative prefractionation methods were determined using liquid scintillation counting. Any surfaces that contacted samples were extracted with 1% SDS to remove any adsorbed or precipitated proteins. Typically, a small volume of these SDS extracts or sample solutions (5 µl) was mixed with 4.5 ml of Bio-Safe II scintillation cocktail (Research Products International Corp, Mt. Prospect, Ill., USA) and radioactivity was counted using a Model 1500 TRI-CARB Liquid Scintillation Analyzer (PACKARD Instrument Company, Downers Grove, Ill., USA). The radioactivity left in gels after elution was counted after solubilization using 1 N NaOH at 60° C. for 3 h, followed by if neutralization with concentrated HCl and addition of the scintillation cocktail.

Example 4
Evaluation of Maximum Protein Loading Capacity without Sample Prefractionation Prior to analysis of prefractionation methods, the effects of different protein loads on resolution and spot detection were evaluated using metabolically radiolabeled *E. coli* extracts. The maximum protein loading capacity of any given 2D gel method is an important parameter since higher protein loading capacities should result in the ability to detect lower abundance proteins for any given gel detection and protein identification thresholds.

Figure 2:
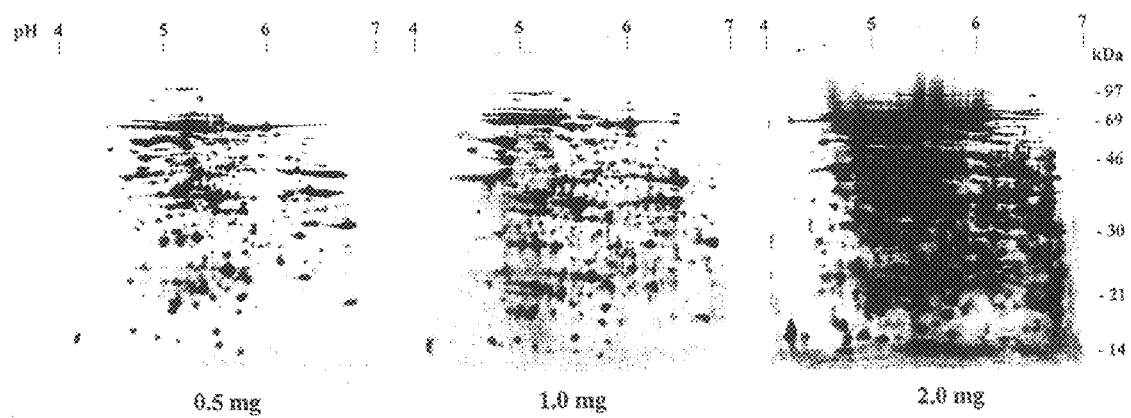
FIG. 2. Demonstrates the effects of increasing protein amounts on 2D PAGE separations of unfractionated *Escherichia coli* extracts. Different amounts of sample were loaded to pH 4–7 L immobilized pH gradient (EPG) strips by rehydration and samples were focused for 60 kVh followed by separation in 10% SDS-gels. Proteins were visualized using Coomassie blue staining. The pH range and location of molecular weight markers are indicated.

About 530 protein spots could be detected on Coomassie blue R250 stained gels when aliquots (0.5 mg protein) of the *E. coli* extracts were separated using 18 cm pH 4–7 L IPG strips and 18 cm long second dimension gels (FIG. 2). The greatest population of protein components fell within the pH 5–6 range where approximately 240 spots were detected. Although most spots were well separated at the 0.5 mg protein load, some horizontal streaking of higher molecular weight and basic proteins was observed. Horizontal streaking, which indicates protein precipitation and/or aggregation, decreases the ability to reliably quantitate the proteins involved, can obscure other proteins underlying the streaking and may induce co-precipitation of other proteins. Further increases in protein load did not substantially increase the number of spots detected, but higher loads (2.0 mg) significantly decreased protein resolution due to both increased horizontal streaking and merging major protein spots with their neighbors. These experiments show that about 1.0 mg of protein was the maximum feasible load of unfractionated *E. coli* extracts for this 2D gel system.

Figure 3:
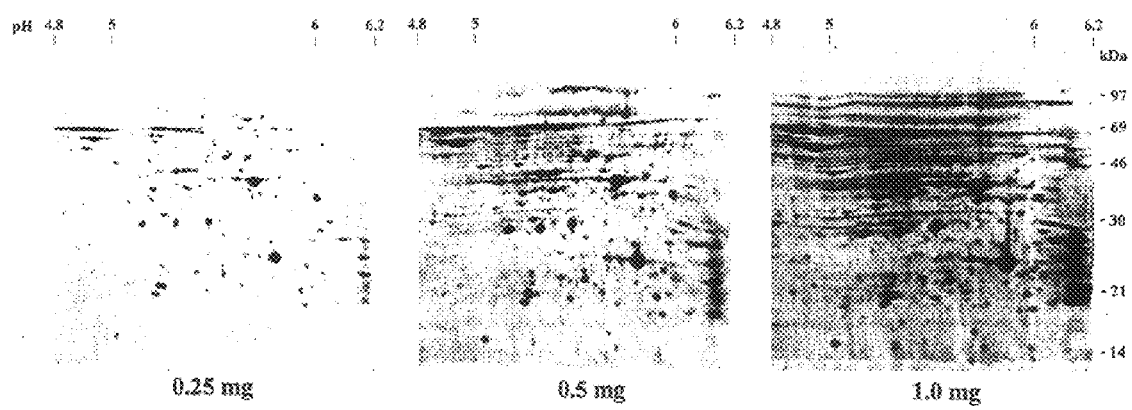
FIG. 3. Shows the separation of unfractionated *E. coli* extracts on narrow pH range IPG-based 2D PAGE. Different amounts of sample were loaded to pH 4.8–6.2 L IPG strips by rehydration and proteins were focused for 60 kVh followed by separation in 10% SDS-gels. Proteins were visualized using Coomassie blue staining.

The maximum protein loading capacity of narrow pH range IPG strips was also evaluated, since one recommended method for improving 2D gel capacities is to separate replicate aliquots of a total cell extract on parallel narrow pH range gels (Herbert et al. (1997) in Proteome Research: New Frontiers in Functional Genomics (Wilkins et al., eds.), pp. 13–33, Springer, Berlin; Wasinger et al. *Electrophoresis* 18, 1373–1383.). The results of separating different amounts of unfractionated *E. coli* extract on pH 4.8–6.2 IPG gels are shown in FIG. 3. Approximately 320 spots were detected in the pH 5–6 range of the gel when 0.25 mg was loaded and separated and most spots were well resolved with moderate horizontal streaking of some higher molecular weight proteins (>60 kDa). Increasing sample loads (0.5 mg and 1 mg) did not substantially increase the total number of protein spots detected, although more severe horizontal streaking was observed, even at lower molecular weights. As expected, the narrower pH range gels (pH 4.8–6.2) increased the total number of spots detected by increasing the resolution within this pH range. For example, the total number of spots between pH 5 and 6 were about 320 in the pH 4.8–6.2 gel when 0.5 mg was separated (FIG. 3), but only about 240 spots were detected when the same sample load was separated in a pH 4–7 gel (FIG. 2). However, the narrower pH gels did not increase the maximum sample load capacity when cell extracts were analyzed without prefractionation.

Therefore, a major disadvantage of existing 2D gel methods when applied to proteome analyses of higher eukaryotes is that the maximum sample loading capacity of whole cell or tissue extracts is fairly low, which results in detection of only the most abundant proteins when currently available stains are used (Herbert et al. 1997; Williams 1999; Quadroni et al. 1999). Increasing the amount of sample above optimal level, e.g. 1–2 mg of the *E. coli* extracts in the present study, results in horizontal streaking of many proteins as shown in FIGS. 2 and 3. Although current IPG-based 2D gels have much higher resolution than alternative separation methods, not all proteins in whole cell extracts can be resolved by a single IPG gel. This incomplete resolution contributes to errors in subsequent quantitation and identification of proteins; that is, a single spot on the gel is frequently not a single protein.

Example 5

Chromatographic Prefractionation of Cell Extracts Prior to 2D PAGE

Several HPLC chromatography methods were initially evaluated as potential prefractionation methods prior to 2D PAGE. HPLC gel filtration in the absence of denaturants resulted in dilute samples and extensive overlap of specific proteins in multiple fractions due in part to the moderate resolution of this chromatographic method and in part to heterogeneous migration of multiple oligomer states. Gel filtration in the presence of denaturants such as urea or SDS primarily separates samples by size similar to the separation that occurs in the SDS gel dimension. This method does not improve the overall capacity of the separation method since the SDS dimension is typically not the limiting factor in 2D PAGE.

Fast protein liquid chromatography (FPLC) ion exchange separation in 7 M urea containing buffers with step pH elutions was attempted in an effort to mimic the separation achieved in the isoelectric focusing dimension. The rationale was that simplifying the sample prior to direct loading onto parallel narrow range IPG gels might minimize precipitation and horizontal streaking. Unfortunately, the volumes required to effectively elute proteins at a given pH step were incompatible with direct application to IPG gels, necessitating concentration of the sample. Losses were high, the method was cumbersome, and resolution at the ion exchange step was inadequate with extensive occurrence of proteins in multiple pools, hence severely complicating quantitative comparisons.

Example 6

Prefractionation of Cell Extracts Using Gel-based Isoelectric Focusing

The incomplete success of the ion exchange chromatography method suggested that the only separation method with adequate resolution to prevent extensive cross contamination of many proteins between multiple pools would be a high resolution isoelectric focusing method closely analogous to the actual analytical IPG gel method itself. While a same-mode prefractionation approach would not improve overall separation by providing a true third mode of separation or 3D method, it offered the potential of improving capacity and resolution when multiple slightly overlapping narrow pH range gels would be used in parallel.

Figure 4:
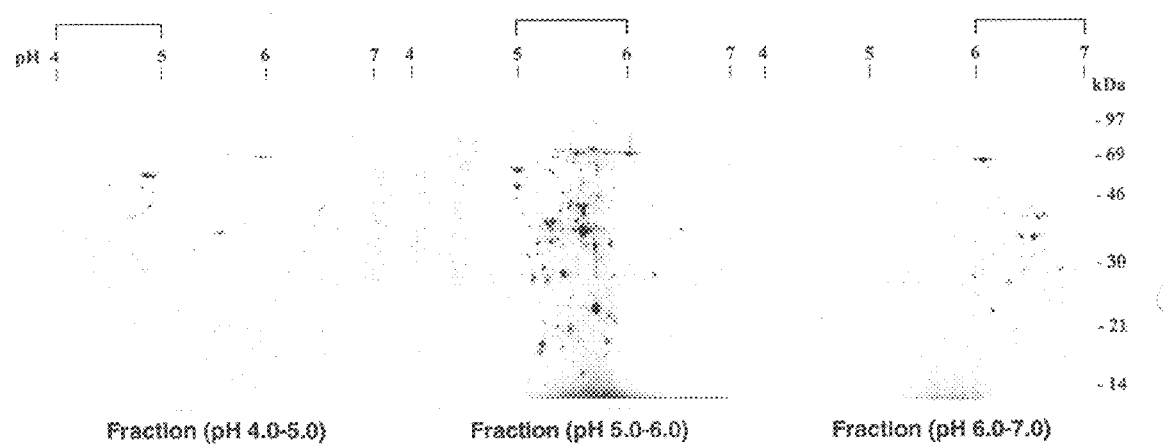
FIG. 4. Demonstrates the evaluation of samples prefractionated using an IPG gel. A 1.0 mg aliquot of *E. coli* extract was initially fractionated on a pH 4–7 L IPG gel, the focused gel was cut into three sections and proteins were eluted. To check the effectiveness of the initial separation, eluted pools were rerun on pH 4–7 L IPG gels for 60 kVh followed by separation in 10% SDS-PAGE gels. Proteins were visualized using Coomassie blue staining. The pH range of the section from the initial IPG gel that was eluted is indicated above each 2D gel by brackets on the pH scale.

To evaluate the feasibility of this approach, 1 mg protein loads of the *E. coli* extracts were initially focused in pH 4–7 L IPG gels. After both ends of the gel that were beyond the electrode locations were removed, the remainder of the gel was cut into three parts having pH ranges of 4–5, 5–6, and 6–7, respectively. The gel sections were separated from the supporting plastic film and each section was extracted with three 500 µl volumes of the IPG sample buffer for 1 h per extraction. The three extractions were pooled (~1.5 ml) and concentrated to about 50 µl using a 10 kDa-cut off Centri-Con® concentration device (Millipore, Bedford, Mass.). The volumes of concentrated samples were adjusted to 350 µl with the IPG sample buffer, loaded to new IPG strips (pH 4–7 L), and analyzed by 2D gel to evaluate the feasibility of an IPG gel-based prefractionation approach (FIG. 4). Typically, all the proteins in the pH 6–7 pool were cleanly separated from other fractions. However, some protein spots recovered in the pH 4–5 and pH 5–6 pools were focused at other pH's when the fractionated samples were refocused on the second IPG strips (FIG. 4). This demonstrated that some proteins failed to focus correctly when the 1.0 mg cell extract sample was initially isofocused in the first 4–7 L IPG gel. This incorrect focusing is consistent with the observed moderate degree of horizontal streaking of some proteins at 1 mg loads described above (FIG. 2).

Losses of sample proteins during prefractionation using IPG gels were impractically high. Typically, about 16% of the total sample protein was recovered in the strip holder after 1.0 mg of *E. coli* extract was initially isofocused using a pH 4–7 L IPG gel with the IPGphor system. The loss of sample proteins at this stage was primarily proteins with pI's outside the pH 4–7 range that ran out of the gel and remained in the strip holder. Another 5.5% of total sample protein was lost in the ends of the IPG gel beyond the electrodes, which contained unfocused proteins and was trimmed off after isoelectric focusing, and 3.6% of the total sample was recovered on the IPG gel plastic supporting film. However, the greatest loss (approximate 23%) resulted from the proteins that were not eluted out of the focused IPG gel fractions after the sequential elutions. The total protein recovery in the three eluted fractions was only about 47% of the original sample applied to the IPG gel. These low recovery and incomplete separation of fractions indicated that a scale up of gel-based isoelectric focusing would not be a practical routine method for prefractionating complex samples prior to 2D PAGE.

Example 7

Prefractionation of Samples by Solution Isoelectric Focusing

Varying numbers of teflon dialysis compartments with 500 μl volumes (Amika Corp, Columbia, Md., USA) were connected in tandem to construct a novel solution isoelectric focusing device used in the following examples. As shown in FIG. 1 this device has three adjacent separation compartments that were separated by 1 mm thick, 3% acrylamide gel membrane partitions containing immobilines at pH 3.5, 5.0, 6.0, and 9.5. Terminal buffer compartments had 10% acrylamide gel membranes for partitions. These terminal buffer compartments were protected from electrode solutions by dialysis membranes (5 kDa cut-off, Amika Corp) and were filled with anode or cathode buffers. O-rings (12 mm i.d.) were used between compartments to assist sealing of gel membranes and compartments by placing an appropriate gel membrane inside an O-ring before the tandem compartments were assembled.

Immobiline gels were cast in different concentrations and thicknesses and with several alternative supports for strength. Typically, Whatman GF/D glass fiber filters were imbedded in the gels for mechanical strength using a BioRad mini-gel plate with 1 mm spacers to cast the gels. Gel solutions were prepared as described in Tables 1 and 2. The 25 ml gel solution volume was sufficient for casting two slab gels (1 mm×7 cm×10 cm). After the gel was polymerized at 60° C. for about 1.5 hour, 12 mm diameter gel membrane discs were excised from the slab gel using a stainless steel core borer. These gel membrane discs were washed three times with 1 ml of Milli-Q water for 1 h per rinse and soaked in the IPG sample buffer for at least 30 min before use. Unused membranes could be stored in the buffer at 4° C. for up to 3 weeks without affecting the effectiveness of sample prefractionation.

TABLE 1

Preparation of Immobiline Mixtures at Desired pH's

| Immobilines | pH 3.5 | pH 5.0 | pH 6.0 | pH 9.5 |
|---|---|---|---|---|
| pK 3.6 | 299 μl | 158 μl | | 410 μl |
| pK 4.6 | 223 μl | 863 μl | 863 μl | |
| pK 6.2 | 157 μl | 863 μl | 803 μl | |
| pK 9.3 | | | 338 μl | 694 μl |
| Water (up to) | 7.5 ml | 7.5 ml | 7.5 ml | 7.5 ml |

The mixture should be within 0.05 pH units of the desired pH. If not, the pH should be adjusted using immobilines.

TABLE 2

Preparation of Gel Membranes

| | 3% T/8% C gel | 10% T/8% C gel |
|---|---|---|
| Immobiline mixture | 7.5 ml | 7.5 ml |
| Acrylamide/Bis (30% T/8% C) | 2.5 ml | 8.33 ml |
| Glycerin (87%) | 3.45 ml | 3.45 ml |
| Ammonium persulfate (40%) | 25 μl | 25 μl |
| TEMED* | 15 μl | 15 μl |
| Water (up to) | 25 ml | 25 ml |

*N,N,N',N'-Tetramethylethylenediamine.

Example 8

Solution Isoelectric Focusing Method for Sample Prefractionation

Figure 5:
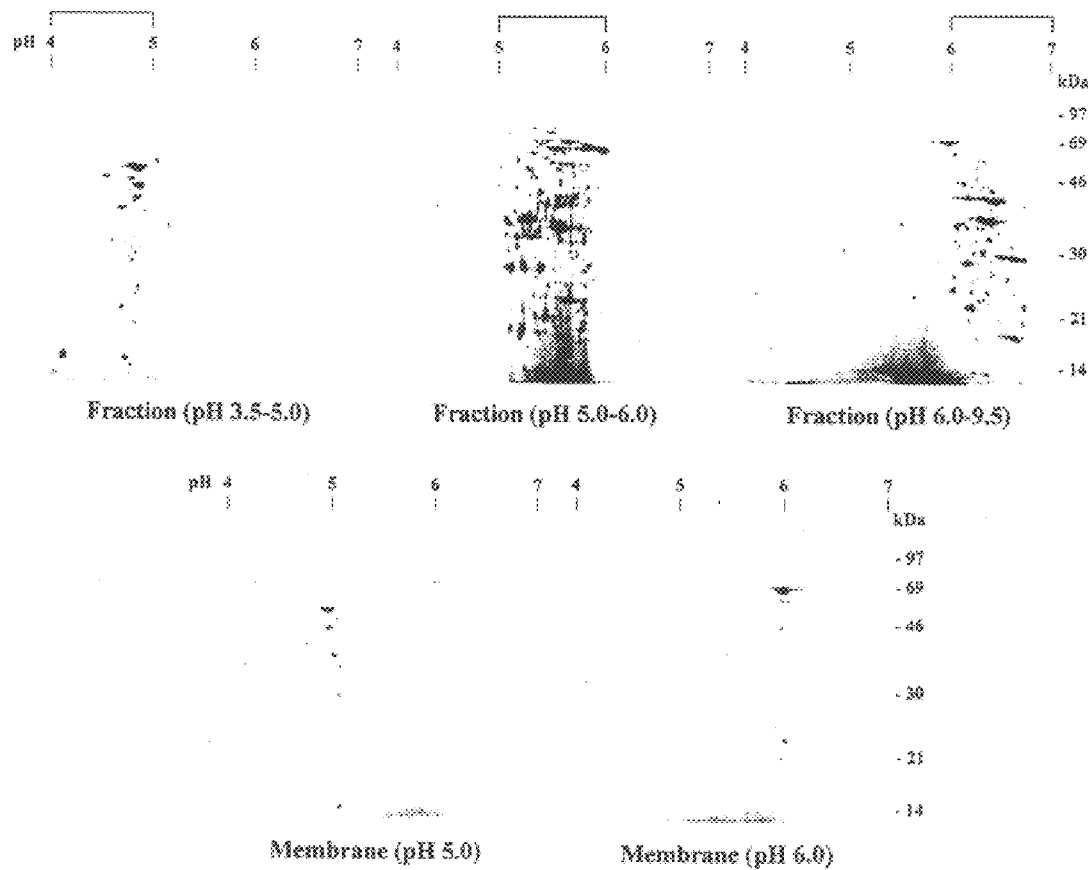
FIG. 5. Shows an evaluation of sample fractionation using solution isoelectric focusing in a representative experiment. Samples from the three separation compartments and the proteins extracted from the separation membranes were evaluated by 2D PAGE after prefractionation of 3 mg of *E. coli* extract using solution isoelectric focusing. One-third of each recovered sample (proportional to 1 mg of original sample) was separated using pH 4–7 L IPG gels followed by separation in 10% SDS-gels. Proteins were visualized using Coomassie blue staining.

An *E. coli* extract (3 mg) was solubilized in 1.5 ml of IPG sample buffer and divided among the three separation compartments of the device described in Example 7. The terminal buffer compartments were filled with BioRad pre-made isoelectric focusing electrode buffers, 7 mM phosphoric acid (anode) and 20 mM lysine/20 mM arginine (cathode). The assembled compartments were placed into the electrophoresis tank (Amika Corp) and the two compartments of the tank were filled with anode and cathode electrode buffers, respectively. A PS500X power supply (Hoefer Scientific Instruments, San Francisco, Calif., USA) was used for focusing the sample. Typically, 100 V was used for 1 h (initial ~2–3 mA, final ~1 mA), followed by 200 V for 1 h (initial ~2–3 mA, final ~1 mA), and then 500 V (initial 3–4 mA) until the current fell to 0 mA (about 1.5 h). After fractionated samples (each ~500 μl) were removed, the surfaces of gel membrane partitions and inside walls of the separation compartments were rinsed with 500 μl of the sample buffer and these rinses were combined with the fractionated samples. The gel membrane partitions were removed and extracted twice with 500 μl sample buffer for 1 h each to elute proteins from the gel matrix. To evaluate the effectiveness of this prefractionation method, one-third of each fractionated sample, which was proportional to 1.0 mg of the original sample, was separated on a pH 4–7 L IPG-based 2D PAGE (FIG. 5). These results showed that the cell extracts were well separated into three discrete pools and only a few overlapping spots were found in the pH 3.5–5.0 and 6.0–9.5 fractions. Only a few proteins were eluted from the membrane partitions and most of them had pI's equal to the membrane pH (FIG. 5).

A composite image (FIG. 6A) of the five individual gels shown in FIG. 5 can be compared to a 2D gel separation of 1.0 mg *E. coli* extract without prefractionation (FIG. 6B). The composite image showed that most protein spots in an unfractionated sample were recovered with good yield in prefractionated samples and resolution was improved (FIG. 6A). Specifically, the total spots in the 2D gel without prefractionation was 545 (FIG. 6B) compared with 610 spots (FIG. 6A) in the prefractionated composite image. More importantly, no horizontal streaking of proteins was observed on the composite image with the prefractionated samples (FIG. 6A), while substantial streaking occurred on the gel with the unfractionated sample (FIG. 6B).

Figure 8:
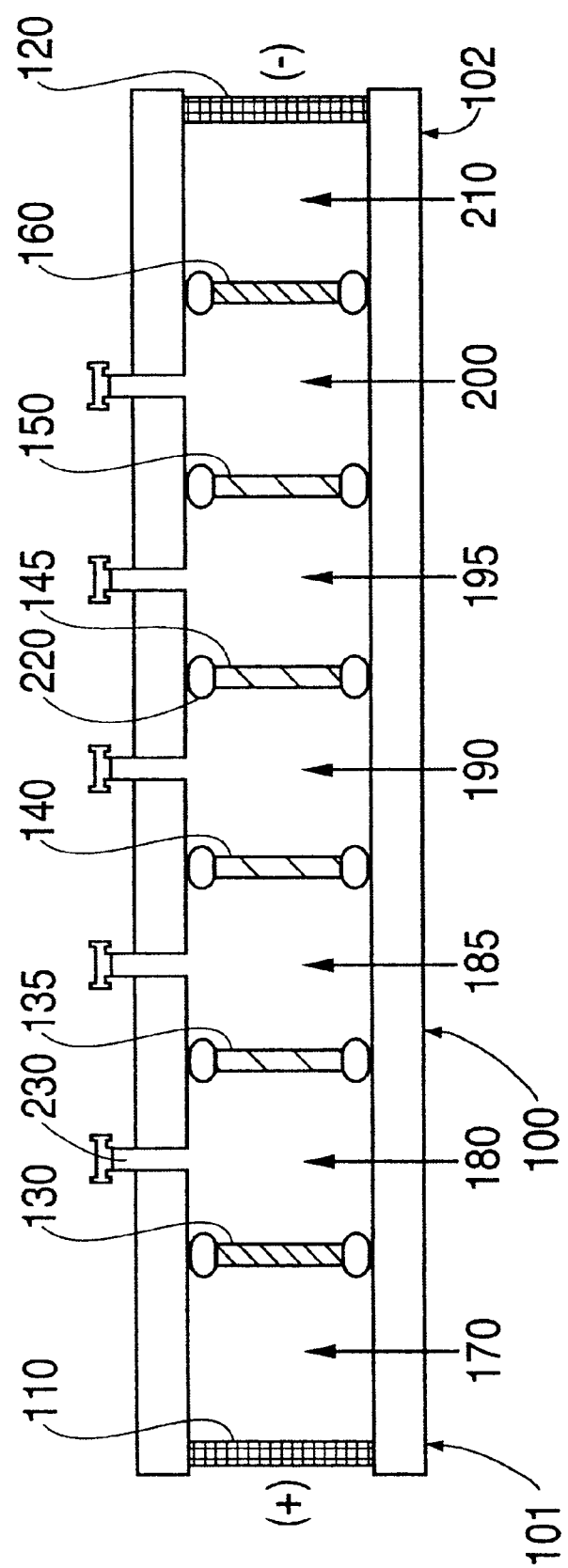
FIG. 8. Demonstrates another isoelectric focusing device of the invention. This device contains more separation compartments than the device of FIG. 1 in order to cover a full pH range. Each compartment has an access port for improved sample loading and removal.

Total protein recovery of the three solution focused fractions was 65% in these experiments. Another 20% of the total sample proteins was associated with the four gel membrane partitions. About three-quarters of the proteins retained in the membranes could be readily extracted and combined with an adjacent fraction to increase overall yield to about 80%. Finally, about 5% of the total sample was found in the two terminal buffer compartments since a small proportion of proteins in the E. coli had pI's outside the pH 3.5–9.5 range of the separation compartments used in these experiments. Most of these proteins can be recovered by modifying the experimental design to cover a wider overall pH range if desired (FIGS. 8, 9).

These experiments demonstrated that this novel device and solution isoelectric focusing method can rapidly separate complex charged molecule mixtures into a small number of discrete well-defined pools in very high yield (>80%) that can be further analyzed by, for example, subsequent separation on parallel slightly overlapping narrow pH gradient gels.

Figure 6:
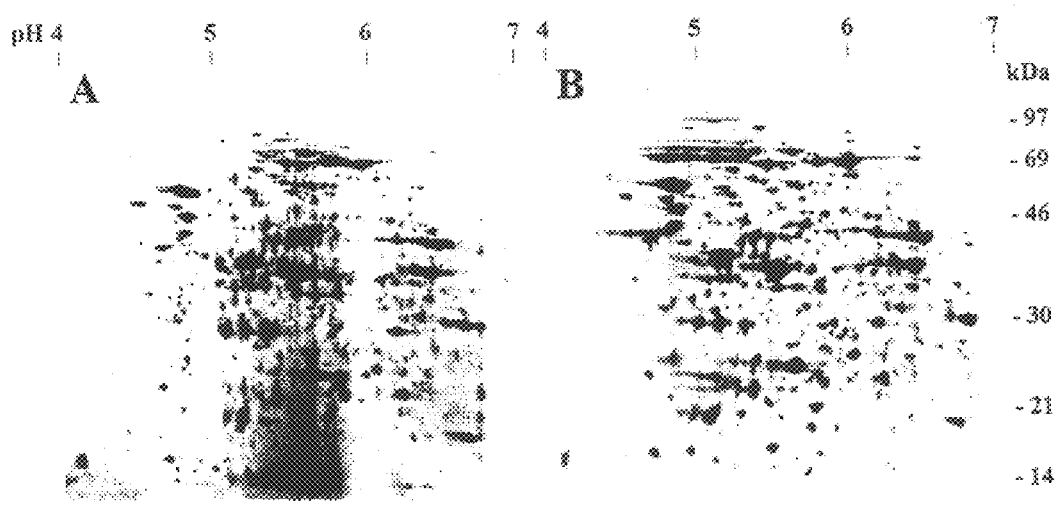
FIG. 6. Shows a comparison of a composite 2D image from prefractionated samples with the 2D image of an unfractionated *E. coli* extract. (A) Composite 2D protein image produced by cutting and pasting the protein containing sections from the five gels shown in FIG. 5. (B) A pH 4–7 L 2D gel containing 1.0 mg of unfractidnated *E. coli* extract. Proteins were visualized using Coomassie blue staining.

Solution isoelectric focusing methods and devices of the invention are much better than eluting proteins from sections of focused IPG gels for prefractionation of samples. Although eluting proteins from a focused IPG gel can result in reasonably well separated fractions, more than 50% of the sample was lost and not all protein spots in the original sample could be recovered after prefractionation (compare FIG. 4 with FIG. 2). In contrast, prefractionation using the methods and devices of the invention results in a higher yield (~80%) and more importantly, most protein spots in the original sample can be recovered (FIG. 6). Initial isoelectric focusing in solution minimizes non-ideal behavior of proteins (precipitation/aggregation) encountered if samples are applied to narrow pH IPG gels without prefractionation (FIG. 3). The fractionated proteins exhibit good solubility when applied to narrow pH range IPG gels, which results in better resolution and more spots detected (FIGS. 5, 6A, 7) compared to direct 2D PAGE without prefractionation (FIGS. 2, 3, 6B). Prefractionation using the method and device of the invention is relatively fast (less than 4 h), requires only a simple, easy-to-use device, and yields well-separated fractions that can be applied directly to subsequent narrow pH IPG strips.

In an initial test of solution isoelectric focusing, 5% gels were used for the separation membranes and 10% gels for the electrode membranes, as suggested for most applications of the IsoPrime™ method (Righetti et al. 1989; Righetti, et al. (1990) *J. Chromatogr.* 500, 681–696; Wenisch et al. (1992) *Electrophoresis* 13, 668–673; Amersham Phamacia Biotech 1999). However, when 1 mm 5% gels were used for separation membranes, many higher molecular weight proteins with pI's not equal to the membrane pH precipitated on the gel matrix, thus resulting in a low overall yield (only ~40%) of fractionated samples and poor separation. When the 5% gels were replaced with 3% gels as separation membranes, the yield and separation of fractions were improved, and typically only proteins with pI's equal to the membrane pH were retained in the 3% gel matrix (see FIG. 5). These results show that even lower gel densities and thinner gel dimensions can be beneficial if the mechanical strength is maintained to prevent membrane rupture during isoelectric focusing. Also, gel membranes can be stored at 4° C. for up to 3 weeks without affecting performance. Longer term storage is feasible if the membranes are dried and frozen for storage similar to the method used to produce commercial IPG strips. The presence of 2% ampholytes in the solution isoelectric focusing is advantageous to effectively focus the sample. The 2 M thiourea/7 M urea present in the sample buffer is superior to 9 M urea alone for solubilizing sample proteins (Rabilloud et al. (1997) *Electrophoresis* 18, 307–316).

The solution isoelectric focusing device (FIG. 1) used in this example had three separation compartments and covered the pH 3.5–9.5 range, where most protein spots occurred in the tested sample used. FIG. 8 demonstrates another embodiment of the invention comprising a chamber (100). A porous charged membrane or a membrane permeable to small ions (110) is located at a first end of the chamber (101). Another porous charged membrane or a membrane permeable to small ions (120) is located at a second end of the chamber (102), opposite of the first end of the chamber (101). Porous charged membrane partitions (130, 135, 140, 145, 150, 160) are positioned along the chamber (100) to define a plurality of compartments (170, 180, 185, 190, 195, 200, 210) within the chamber (100). The porous charged membrane partitions can comprise, for example, pH's of 2.5, 5.0, 5.5, 6.0, 7.5, and 11. The porous charged membrane partitions (130, 135, 140, 145, 150, 160) are each fitted into the chamber (100) with a seal (220). An access port (230) provides access to each compartment. The larger number of compartments and wider pH range of this device will be appropriate for comprehensive or global analyses of complex eukaryotic proteomes. The volumes of separation compartments can be adjusted to fit experimental design such that fractionated sample volumes match the IPG gel rehydration volumes for the number of replicate 2D gels desired. Similarly, the total number of separation compartments and the pH's of membrane partitions can be altered to fit requirements of specific studies.

Example 9
Effects of Narrow pH Range IPG Gels on Protein Detection and Resolution The feasibility of using narrow pH gradient gels with samples prefractionated using the device and method of the invention was evaluated. Replicate fractionated samples (pH 5–6) prepared by solution isoelectric focusing were separated on different pH range IPG strips (pH 3–10 NL, 4–7 L and 4.8–6.2 L) followed by SDS-PAGE (FIG. 7). The protein spots in the 2D gels were found only within the pH 5 to 6 range regardless of IPG gel pH ranges or detection methods used. These results verify that the components in the pH 5–6 fractionated sample were well resolved from other pH fractions with no detectable cross-contamination of proteins after the prefractionation step even when the more sensitive autoradiography detection method was used (FIG. 7). The advantage of using narrow pH gradient gels with sample prefractionation was clearly demonstrated by the improved resolution of a fractionated pool on narrow pH range gels. Specifically, about twice as many protein spots were detected on an 18 cm pH 4.8–6.2 L gel compared with a pH 3–10 NL gel with either Coomassie Blue detection (355 spots vs. 187 spots) or the more sensitive autoradiographic detection (543 spots vs. 281 spots).

The advantages of prefractionation are further illustrated by comparing the 2D gels using pH 4.8–6.2 L IPG strips to the 2D PAGE analysis of unfractionated samples using the same narrow pH range (FIG. 3 and FIG. 7). No horizontal streaking of proteins was observed on the 2D gel with prefractionation (FIG. 7), but substantial horizontal streaking occurred on 2D gels loaded with 1.0 mg of unfractionated samples (FIG. 3). Prefractionation using solution isoelectric focusing eliminates interfering components with pI's beyond the pH range of a given narrow IPG gel which otherwise may precipitate or aggregate in the gel. Hence, the prefractionation step results in overall load capacity increases over alternative 2D PAGE methods such as direct use of parallel narrow pH range gels without prefractionation. Increased sample loads without precipitation or aggregation using this system can improve the reliability of quantitative comparisons, increase the number of spots that can be resolved and allow detection of lower abundance spots. Finally, prefractionation more effectively utilizes samples that are available in limited amounts compared with replicate application of unfractionated samples to multiple different narrow pH range gels.

Example 10

Characterization of Protein Mixtures Prefractionated by Solution Isoelectric Focusing Using Mass Spectrometry Methods Protein mixtures that are prefractionated using solution isoelectric focusing into at least 2, and preferably 5, 10, 50 or more discrete fractions can be further analyzed by fragmenting the protein mixture using either proteases or chemical cleavage followed by analysis of the fragments using mass spectrometry (MS) methods.

For example, one or more protein mixtures are fractionated using solution isoelectric focusing as described above, except that the concentration of the detergent is decreased from 4% to 0.5% and separation compartment volumes of 200 µl are used. After isoelectric focusing, samples are removed from individual separation compartments, the separation chamber is rinsed with 50 µl of wash buffer (100 mM Tris, 9 M urea, pH 8.2), the adjacent membrane partitions are extracted twice with 75 µl wash buffer for 1 hr each. The extracts are combined with the original sample. The pH is adjusted to pH 8.2 using NaOH, iodoacetamide is added to a final concentration of 0.2 M, and the sample is incubated in the dark for 30 min at room temperature to modify cysteines. The protein sample is diluted 3-fold by adding 0.8 ml 100 mM Tris-Cl pH 8.2, proteins are cleaved at lysines and arginines by addition of sequence grade trypsin in solution using conditions determined to cleave most lysines and arginines, for example, using an enzyme:substrate ratio of 1:50 by weight for 4 hr at 37° C. To obtain effective trypsin digestion, it is essential that the urea concentration be decreased to a concentration compatible with effective enzyme activity such as the 3M final concentration described here. Alternatively, the protein sample can be cleaved by circulating the protein through a column containing covalently coupled trypsin (PE Biosystems or MoBeTec) using methods described by the manufacturers and known to one skilled in the art.

After digestion, the pH of the sample is lowered to 2.0 using trifloroacetic acid, an aliquot of the sample (typically 5–10%) is loaded onto a capillary C18 reverse phase column, and the column is extensively washed with 0.1% acetic acid to remove any remaining soluble reagents from prior steps. The column is then introduced into the flow pathway of a capillary HPLC interfaced with a mass spectrometer equipped with an electrospray interface such as the Finnigan LCQ ion trap mass spectrometer. Peptide masses and MS-MS spectra are obtained by established methods, and are used to identify the proteins utilizing database search algorithms such as the program SEQUEST.

We claim:

1. A chamber for holding a liquid, the chamber having a first porous charged membrane partition or a first membrane permeable to small ions at a first end, a second porous charged membrane partition or a second membrane permeable to small ions at a second end which is opposite the first end, and porous charged membrane partitions positioned along the chamber to define a plurality of compartments within the chamber such that each compartment holds a volume of liquid less than about 4 ml wherein each porous charged membrane partition comprises a different pH.

2. The chamber of claim 1 wherein each porous charged membrane partition comprises an inorganic or an organic membrane.

3. The chamber of claim 2 wherein each porous charged membrane partition comprises polyacrylamide.

4. The chamber of claim 3 wherein the chamber comprises a plurality of porous charged membrane partitions and the porous charged membrane partition adjacent to the first porous charged membrane partition or the first membrane permeable to small ions at the first end of the chamber and the membrane partition adjacent to the second porous charged membrane partition or the second membrane permeable to small ions at the second end of the chamber comprise a higher percentage of polyacrylamide than the remaining porous charged membrane partitions.

5. The chamber of claim 2 wherein each porous charged membrane partition comprises covalently linked buffering groups.

6. The chamber of claim 1 comprising at least 5 porous charged membrane partitions.

7. The chamber of claim 1 wherein the area of each porous charged membrane partition is between about 5 and 200 mm$^2$.

8. The chamber of claim 1 wherein the area of each porous charged membrane partition is about 100 mm$^2$.

9. The chamber of claim 1 wherein the chamber further comprises an access port for each compartment.

10. The chamber of claim 1 wherein each compartment holds a volume of liquid less than about 2 ml.

11. The chamber of claim 1 wherein each compartment holds a volume of liquid less than about 1 ml.

12. The chamber of claim 1 wherein each compartment holds a volume of liquid of from about 0.5 ml to about 1 ml.

13. The chamber of 1 which contains at least 10 compartments to permit separating a mixture of at least ten species of charged molecules in liquid.

14. The chamber of claim 13 wherein each porous charged membrane partition comprises an inorganic or an organic membrane.

15. The chamber of claim 14 wherein each porous charged membrane partition comprises polyacrylamide.

16. The chamber of claim 15 wherein each porous charged membrane partition comprises covalently linked buffering groups.

17. The chamber of claim 13 wherein each porous charged membrane partition comprises a different pH.

18. An apparatus for separating charged molecules comprising an apparatus selected from the group consisting of:
   (i) the chamber of claim 1, an electrophoresis tank, and a power source;
   (ii) the chamber of claim 1 and an electrophoresis tank; and
   (iii) the chamber of claim 1 and a power source.

19. A method of separating a mixture of charged molecules comprising the steps of:

adding a mixture of charged molecules in solution to the chamber of claim 1; and applying a direct current between the first end and the second end of the chamber while said solution is held in said chamber, whereby the charged molecules are separated.

20. The method of claim 19 wherein the charged molecules are separated according to their isoelectric points.

21. The method of claim 19 wherein an anode buffer is placed in the compartment of said chamber having the first porous charged membrane partition or the first membrane permeable to small ions as a partition; and a cathode buffer in the compartment of said chamber having the second porous charged membrane partition of the said membrane permeable to small ions as a partition.

22. The method of claim 19 wherein the charged molecules are proteins.

23. The method of claim 22 wherein at least about 10 protein species are added.

24. The method of claim 22 wherein at least about 100 protein species are added.

25. The method of claim 22 wherein the proteins comprise a sample selected from the group consisting of a prokaryotic proteome, a eukaryotic proteome, a cell sample, a tissue sample, a fractionated cell sample, a fractionated tissue sample, and a biological fluid.

26. A chamber for holding a liquid, the chamber having a first porous charged membrane partition or a first membrane permeable to small ions at a first end, a second porous charged membrane partition or a second membrane permeable to small ions at a second end which is opposite the first end, and at least one porous charged membrane partition positioned along the chamber to define a plurality of compartments within the chamber such that each compartment holds a volume of liquid less than about 4 ml, said chamber further comprising an access port with a removable cap for each compartment.

27. A method of separating a mixture of at least about 10 species of charged molecules in liquid comprising the steps of:

adding the charged molecules to a chamber for holding liquid having a first porous charged membrane partition or a first membrane permeable to small ions at a first end, a second porous charged membrane partition or a second membrane permeable to small ions at a second end which is opposite the first end, and at least one porous charged membrane partition positioned along the chamber to define a plurality of compartments within the chamber, each compartment holding a volume of liquid less than about 4 ml; and applying a direct current between the first end and the second end of the chamber while said liquid is held in said chamber, whereby the charged molecules are separated.

28. The method of claim 27 comprising a mixture of at least about 100 species of charged molecules.

29. The method of claim 27 wherein the charged molecules are separated according to their isoelectric points.

30. The method of claim 27 wherein the charged molecules are proteins.

31. The method of claim 30 wherein the proteins comprise a sample selected from the group consisting of a prokaryotic proteome, a eukaryotic proteome, a cell sample, a tissue sample, a fractionated cell sample, a fractionated tissue sample, and a biological fluid.

32. A method of two-dimensional electrophoresis comprising the steps of:

(a) separating a mixture of charged molecules by the method of claim 19 or 27; and (b) subjecting the separated charged molecules of step (a) to gel electrophoresis.

33. A method of two-dimensional electrophoresis comprising the steps of:

(a) separating a mixture of charged molecules by the method of claim 19 or 27;

(b) further separating charged molecules of step (a) using gels selected from the group consisting of immobilized pH gradient gels and ampholyte based isoelectric focusing gels; and (c) subjecting the separated charged molecules of step (b) to gel electrophoresis.

* * * * *